United States Patent
Renner et al.

(10) Patent No.: US 11,116,950 B2
(45) Date of Patent: Sep. 14, 2021

(54) STENT FOR SPLINTING A NASAL PASSAGE

(71) Applicant: Klaus Duering, Frechen (DE)

(72) Inventors: Peter Renner, Bergheim (DE); Klaus Duering, Frechen (DE); Joachim Georg Pfeffer, Aachen (DE); Nasib Dlaikan-Campos, Wuerselen (DE)

(73) Assignee: Klaus Duering, Frechen (DE)

( * ) Notice: Subject to any disclaimer, the term of this patent is extended or adjusted under 35 U.S.C. 154(b) by 298 days.

(21) Appl. No.: 16/111,737

(22) Filed: Aug. 24, 2018

(65) Prior Publication Data

US 2018/0361129 A1 Dec. 20, 2018

Related U.S. Application Data

(63) Continuation of application No. 13/983,028, filed as application No. PCT/EP2012/000589 on Feb. 9, 2012, now abandoned.

(30) Foreign Application Priority Data

Feb. 9, 2011 (DE) .................. 102011010754.1

(51) Int. Cl.
A61F 5/56 (2006.01)
A61F 2/90 (2013.01)
A61M 29/02 (2006.01)
A61F 5/08 (2006.01)

(52) U.S. Cl.
CPC .............. A61M 29/02 (2013.01); A61F 5/08 (2013.01); A61F 5/56 (2013.01); A61F 2/90 (2013.01); A61F 2210/0076 (2013.01); A61F 2220/00 (2013.01); A61F 2230/0071 (2013.01)

(58) Field of Classification Search
CPC ........ A61B 17/12022; A61B 17/12168; A61B 17/1214; A61B 17/12172; A61B 17/12131; A61F 2/82; A61F 2/86; A61F 2/88; A61F 2/89; A61F 2/90; A61F 5/08; A61F 5/56; A61F 2002/821; A61F 2002/823;
(Continued)

(56) References Cited

U.S. PATENT DOCUMENTS

| 5,246,445 | A | 9/1993 | Yachia et al. |
| 5,336,163 | A | 8/1994 | DeMane et al. |
| 8,241,316 | B2 | 8/2012 | Oberle |

(Continued)

FOREIGN PATENT DOCUMENTS

| CA | 2632420 A1 | 6/2007 |
| DE | 2141252 A1 | 2/1973 |

(Continued)

Primary Examiner — Majid Jamialahmadi
(74) Attorney, Agent, or Firm — Hultquist, PLLC; Steven J. Hultquist

(57) ABSTRACT

The present invention relates to a stent for splinting a nasal passage. The stent consists of a braided tubular support body which, in unloaded state, has a diameter of at least 4 mm and a length in the range of 25 to 120 mm and particularly of 25 to 100 mm. The stent may have a widened section at the proximal end for splinting of the nasal alar. It may alternatively or in combination have a fixation section at the proximal end of the stent for fixation of the stent in a nasal passage of a user. When fixed the fixation section protrudes from the nostril of the user and can be fixed outside of the nose.

20 Claims, 12 Drawing Sheets

Figure 1:
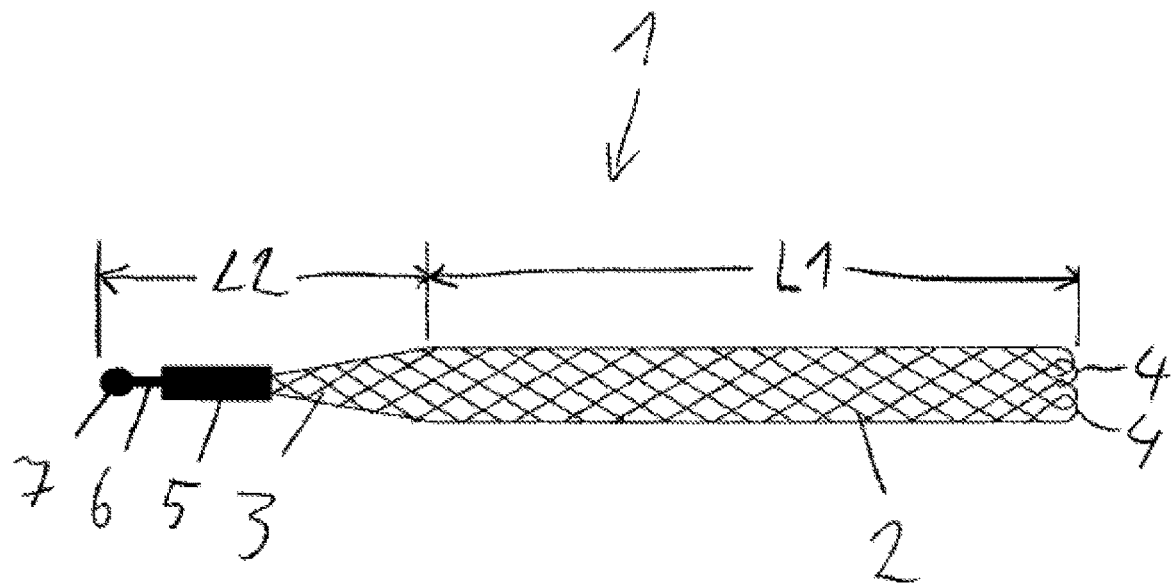

(58) Field of Classification Search
CPC .......... A61F 2002/825; A61F 2002/826; A61F 2002/828
USPC ........................................................ 606/199
See application file for complete search history.

(56) References Cited

U.S. PATENT DOCUMENTS

| | | |
|---|---|---|
| 2003/0144725 A1 | 7/2003 | Lombardi |
| 2005/0197690 A1 | 9/2005 | Molaei et al. |
| 2006/0249161 A1 | 11/2006 | Waters et al. |
| 2007/0179590 A1 | 8/2007 | Lu et al. |
| 2007/0198075 A1* | 8/2007 | Levy ................. A61F 2/82 623/1.11 |
| 2009/0010991 A1 | 1/2009 | Prabhu et al. |
| 2009/0287294 A1* | 11/2009 | Rosqueta ......... A61B 17/12113 623/1.15 |
| 2010/0106255 A1 | 4/2010 | Dubin |
| 2010/0211181 A1 | 8/2010 | Prabhu et al. |
| 2010/0319708 A1 | 12/2010 | Mahr et al. |
| 2012/0143345 A1 | 6/2012 | Duering et al. |

FOREIGN PATENT DOCUMENTS

| | | |
|---|---|---|
| DE | 202009010388 U1 | 1/2011 |
| WO | 03092765 A2 | 11/2003 |
| WO | 2007065408 A2 | 6/2007 |
| WO | 2011012320 A2 | 2/2011 |

* cited by examiner

STENT FOR SPLINTING A NASAL PASSAGE

CROSS-REFERENCE TO RELATED APPLICATIONS

This is a continuation under 35 USC § 120 of U.S. patent application Ser. No. 13/983,028 filed Jul. 31, 2013, which in turn is a U.S. national phase under the provisions of 35 U.S.C. § 371 of International Patent Application No. PCT/EP12/00589 filed Feb. 9, 2012, which in turn claims priority of German Patent Application No. 102011010754.1 filed Feb. 9, 2011. The disclosures of U.S. patent application Ser. No. 13/983,028, International Patent Application No. PCT/EP12/00589, and German Patent Application 102011010754.1 are hereby incorporated herein by reference in their respective entireties, for all purposes.

The present invention relates to a stent for splinting a nasal passage.

Under the trade name "Schnarchzapfen" plastic splints for splinting of the nostrils are provided. The plastic splints each consist of several plastic rings which are connected by longitudinal struts. At one end two of these plastic splints are connected to each other by a plastic holder so that the two plastic splints can be inserted in the two nostrils. At the ends connected by the plastic holder the diameter of the plastic splint is larger than at the end distal from the holder. Thus, these splints are inserted into the nose with the thinner end ahead. These splints are about 10 mm long and ensure that the nose in the region of its opening is kept open.

Under the brand name Nasaline® nasal dilators are provided which expand the nasal alars and thereby shall reduce mouth breathing. Such nasal dilators are short plastic bushings which are loosely interconnected so that their distance is adjustable.

These products "Schnarchzapfen" and Nasaline® are each bushing-type or tubular bodies which shall keep open the nasal alars.

Instead of such bushing elements also wings exist with which the nasal alars are pushed apart. One such element with two spacer wings which are fixed in a preset distance by a stiff nasal holder made from titanium is known under the brand name Nasanita Nasenschmetterling®. Another element for maintaining patency of the nasal alars relying on the same mode of action is sold under the brand name Nozovent®.

The above described apparatuses serve for maintaining patency of the nostrils.

The company MBM ScienceBridge GmbH, Göttingen, Germany has developed a nasopharyngeal splint. This splint consists of two plastic splints which each is shaped synclinally whereas the synclinal splints are interconnected at one end by an elongated holder. Each splint can be introduced in one nostril. The splints are shaped in a way that they can be introduced through the nose, passed along the nasal septum and keep open the upper throat by their shape. The soft palate is prevented to close the throat. Thereby, a continuous breathing shall be ensured. In snoring therapy the splints are onetime adapted for the patient by endoscopy. This is necessary in order to ensure that the length of the splint is exactly adjusted.

WO 2007/065408 A2 discloses an apnea stent which serves for splinting and/or keeping open the airway in the throat. This apnea stent consists of a compressible and self-expanding stent which exhibits at least one expanded section. This stent consists of three phases. A distal phase of the stent provides the active part of the apnea stent. This distal phase has a tubular shape and expandable in a way so that the airway is kept open. A proximal phase of the stent is provided for fixing the stent in the nasal area. The proximal phase is funnel-shaped whereas this phase widens from the proximal towards the distal end. The distal and the proximal phase are made as a braid in which the wires or fibers or strands, respectively cross each other. Each individual wire directed to the distal end of the stent at the distal end of the distal phase is returned to the proximal end of the stent. The bends created in this way are referred to below as round ends. A transition phase of the stent is intended for the connection of the proximal phase with the distal phase. The transition phase is formed by twisting of the wires of the stent into twisted strands. As a result the transition section exhibits a high flexibility in radial direction so that within a short longitudinal stretch a strong radial expansion from the proximal to the distal phase is effected.

DE 20 2009 010 388 U1 and PCT/EP 2010/004687, respectively, disclose a fixing device for fixation of such an apnea stent in the airway wherein the fixing device exhibits two clamping elements between which the proximal end of the apnea stent can be fixed. Further, an introduction tube for introduction of the apnea stent is described which is bent at its distal end in order to simplify the introduction into the airway. The apnea stent exhibits at its proximal end a connecting and coupling element so that an inserting rod can be fixed at the proximal end of the apnea stent. By means of the inserting rod the stent can be introduced into the introduction tube 6 and be compressed by pushing the inserting rod through the introduction tube so that the apnea stent is pulled by the inserting rod into the introduction tube.

U.S. Patent Application Publication 2009/0010991 A1 discloses an expandable nasal stent which is permanently inserted into the nostril or the nasal passage. This stent is made from a polymer or steel grid and equipped with a filter element which is positioned at the proximal end of the stent. The stent can be coated with a therapeutic agent.

U.S. Patent Application Publication 2010/0211181 A1 and U.S. Pat. No. 5,336,163 disclose further nasal stents which are constructed as filters for filtering the inhaled air.

U.S. Patent Application Publication 2010/0106255 A1 discloses a self-expanding stent which can be anchored with one end in the sinus.

The present invention is based on the object to provide a stent for splinting of a nasal passage which does not need to be individually adjusted for each nasal passage, it shall be easily introduced and comfortable in use, and it shall fully and reliably keep open a nasal passage.

This object is achieved by a stent comprising the features of claim 1. Advantageous embodiments are indicated in the sub-claims.

The stent for splinting of a nasal passage according to the present invention consists of a braided tubular support body and optionally a fixation section. The support body in unloaded state has a diameter of at least 4 mm and a length in the range of 25 to 120 mm and particularly of 25 to 100 mm.

At the proximal end of the stent a fixation section can be provided which is designed for fixation of the stent in the nasal passage of the user wherein the fixation section extends out of the nostril of the user when fixing and can be fixed outside of the nose.

The braided support body is elastically deformable and nestles to the inner surface of the nasal passage. The pressure created by the tubular support body against the nasal passage evenly scatters, and therefore the support body does not cause any pain or unpleasant feeling in the sensitive nasal passage. As the support body is braided it nestles well to different shapes of the nasal passage and it is not necessary to individually adapt the stent to the nasal passage of an individual user. With a few standard sizes of the stent which mainly differ in length and diameter of the support body for almost any person a suitable stent can be provided. The support body can be provided with diameters of 4 to 20 mm whereas the standard sizes preferably differ in the diameter and are staggered in 1 mm steps. The length of the support body is in the range of 25 mm to 120 mm and particularly 25 to 100 mm. Preferably the standard sizes differ in length, staggered in 5 mm steps.

The preferred length of the support body is in the range of 30 mm to 50 mm as this is the usual length of the nasal passage in the region of the anterior turbinates for average body sizes.

It has turned out that for most users a support body with a length of about 60 mm is positioned with its distal end in an area of the nasal passage and turbinates which is highly sensitive. Therefore it is useful to provide a support body with either a shorter length so that it is not in contact with this sensitive area, or with a greater length so that it extends along this sensitive are. Therefore, on the one hand support bodies with a length of maximally 40 to about 45 or 50 mm, respectively, or support bodies with a length of at least 70 to 80 mm or 100 mm, respectively are preferred.

The function of the fixation section lies in the prevention that the support body moves along the nasal passage in direction to the throat. The fixation section therefore is connected to the support body and extends to the outside of the nose. There, the fixation section can be fixed.

The fixation section can be designed one-piece with the support body as a braided tubular section tapered towards the proximal end. The fixation section can also be made from any desired other material which preferably is flexible.

A coupling element is provided at the proximal end of the fixation section which can be connected to a mating coupling element of an inserting rod or a holding element. The mating coupling element is provided at one end of the inserting rod. The stent can be introduced into an introduction tube and compressed with the stent coupled to the inserting rod. For that purpose the inserting rod is pushed through the introduction tube so that the stent is pulled into the introduction tube by the inserting rod.

Preferably the holding element provides two mating coupling elements for coupling of two proximal elements of two stents to the coupling element. Thereby, the coupling element provides a detachable holder between the two stents which securely prevents movement of the stents too far in direction to the throat.

The coupling element also can be provided as a clamp which fixes the fixation section of a stent or two fixation sections of two stents by clamping. The clamping can be executed independent of the coupling element for coupling of the stent to an inserting rod or, alternatively, by clamping of the coupling element in the holding element.

The stent can be braided from wires, fibers and/or strands which cross each other. In the following only the term wire is used whereas this includes also fibers or strands as far as the wire is not further specified.

Each individual wire directed towards the distal end of the stent is returned at the distal end of the support body towards the proximal end of the stent. The bends resulting from that are referred to below as round ends. These have in unloaded state of the stent a diameter in the range of 0.5 to 2 mm. Thereby a distal end is provided without any individual free wire ends or no free wire ends need to be connected with another element. The connection of the wire or the wires, respectively, of the stent at the proximal end can be simply realized e.g. by crimping or gluing so that a fixation section is created. Alternatively, the wires also can be connected e.g. by a droplet of polymer, a ring, or by returning them into the inner lumen of the support body without creating a fixation section. The round ends prevent injury of the airways caused by the distal end of the stents.

The wire used for braiding of the support body particularly is a metal wire, preferably a nitinol or steel wire.

Preferably the distal end of the support body, most preferably only the round wires, are provided slightly tapered relative to the other part of the support body. This prevents that the stent may press with its ending border into the nasal passage which may be uncomfortable.

The support body can be provided at its proximal end with a widened section. This widened section preferably has about a ball-shape. The ball has a diameter of about 10 to 20 mm, preferably 12 or 13 to 15 or 17 mm, respectively This widened section of the support body during use is positioned in the region directly behind the nostrils in order to splint the nasal alar to prevent a collapse. Additionally, the widened section fixes the stent in the nose so that especially for a stent comprising a widened section the above described fixation section may not be necessary. Such a stent is most useful for sports during which the nasal passages shall be kept open. A fixation section protruding from the nose is undesirable during sports.

It is useful to provide a removal tool for stents without a fixation section with which the stent can be removed from the nasal passage. The removal tool can be coupled with the stent, e.g. by providing an element for hooking into the braid of the stent or an element for grasping the braid. For coupling to the removal tool solely the braided support body is sufficient. For that purpose no additional part needs to be provided at the stent.

Figure 2:
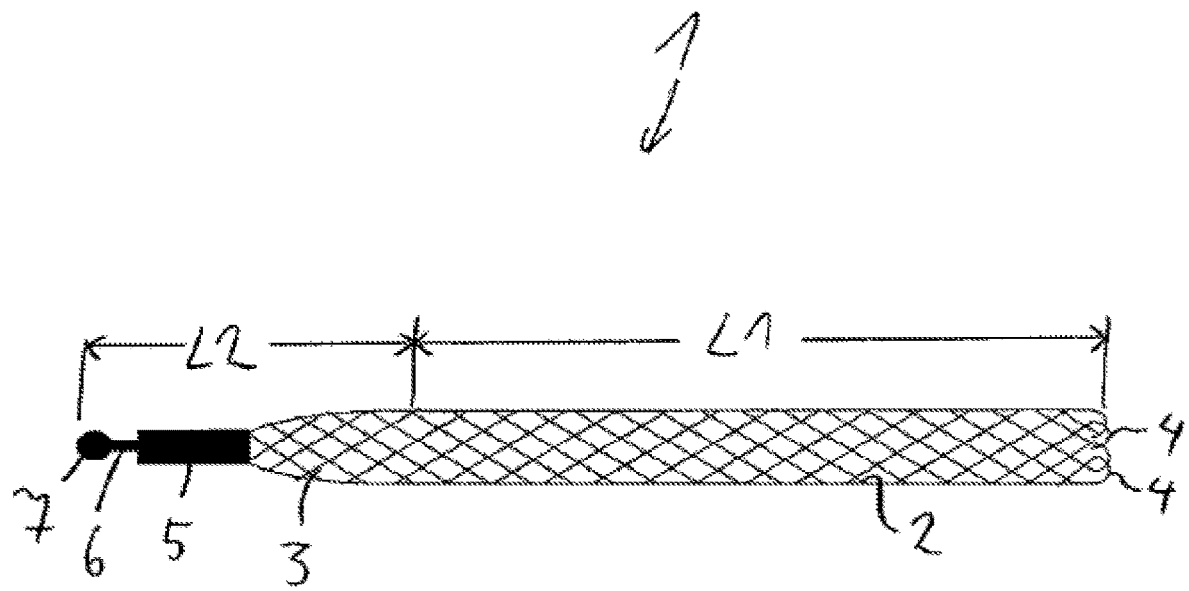
Figure 3A:
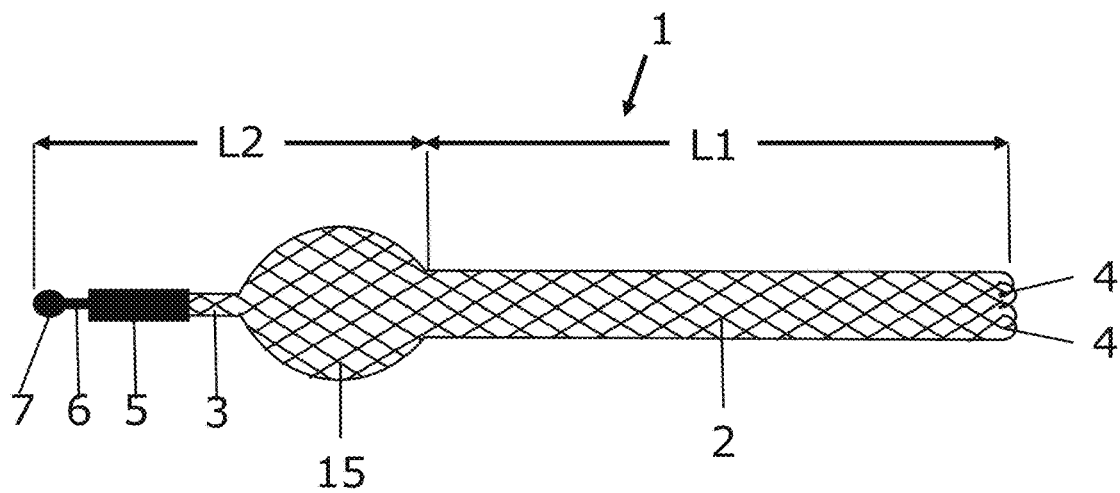
Figure 3B:
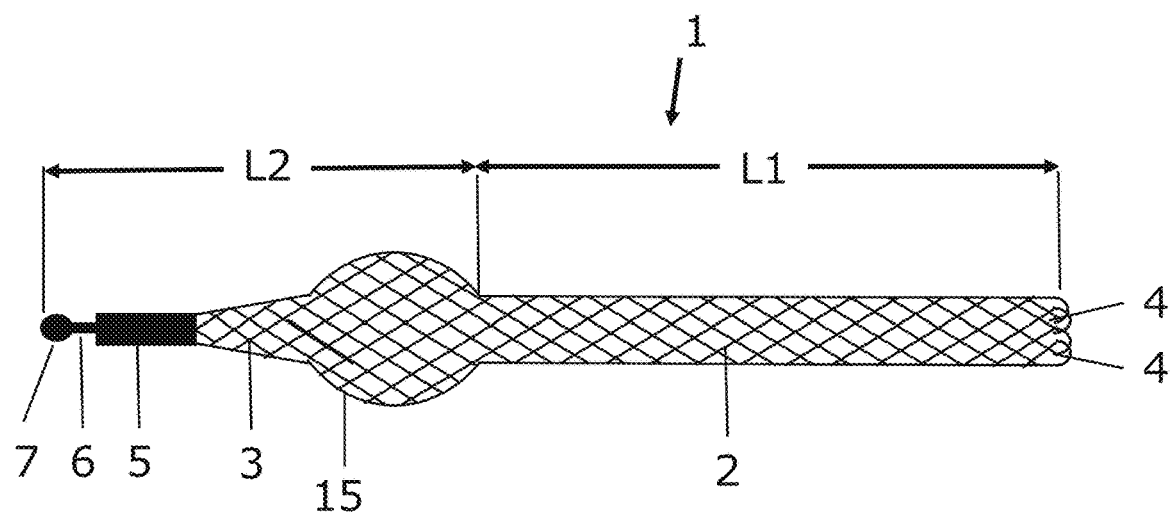
Figure 4:
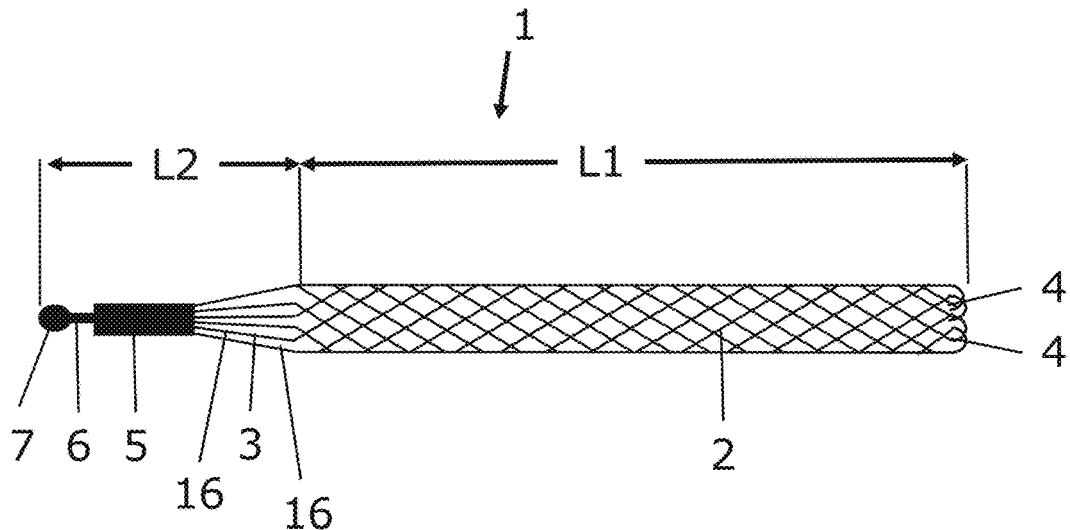
Figure 5A:
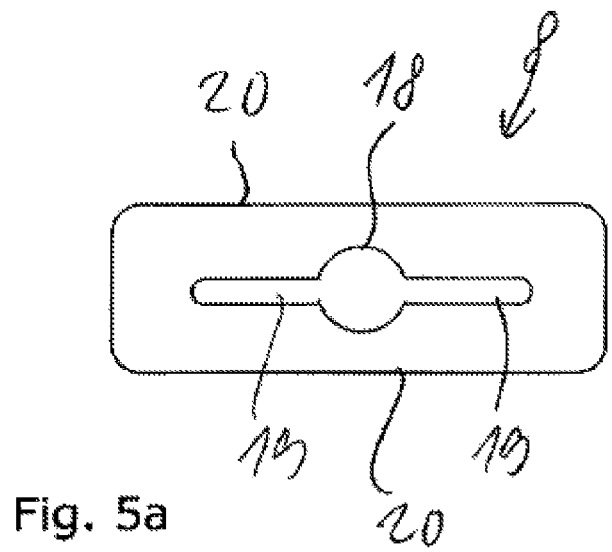
Figure 5B:
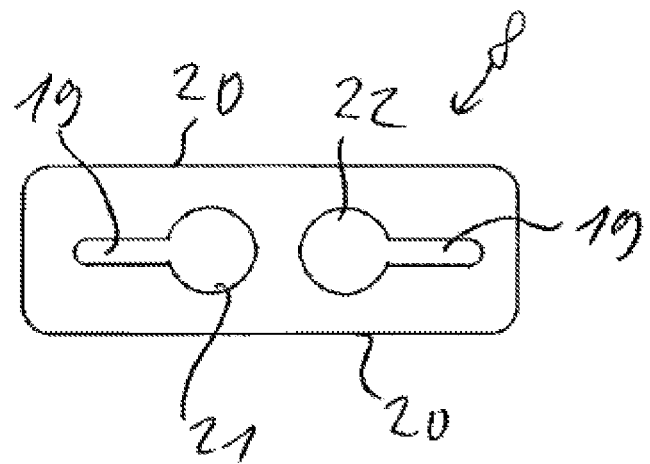
Figure 6:
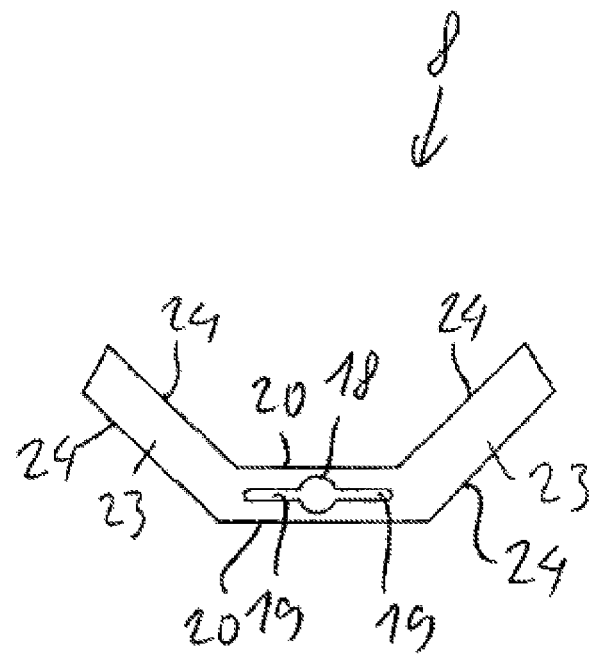
Figure 7A:
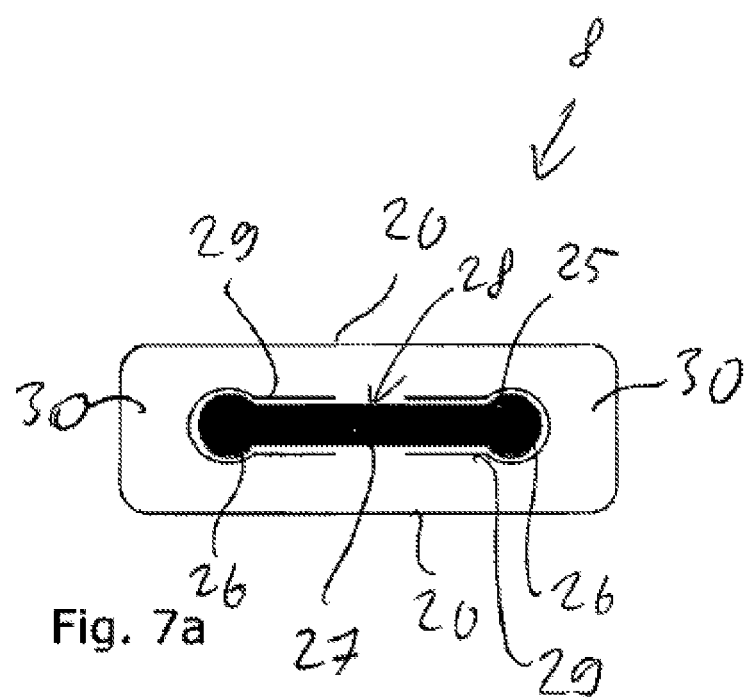
Figure 7B:
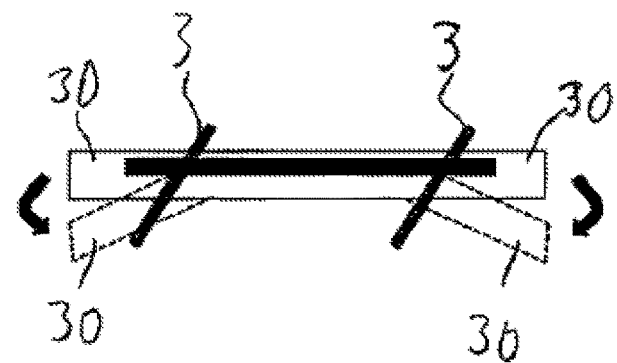
Figure 8:
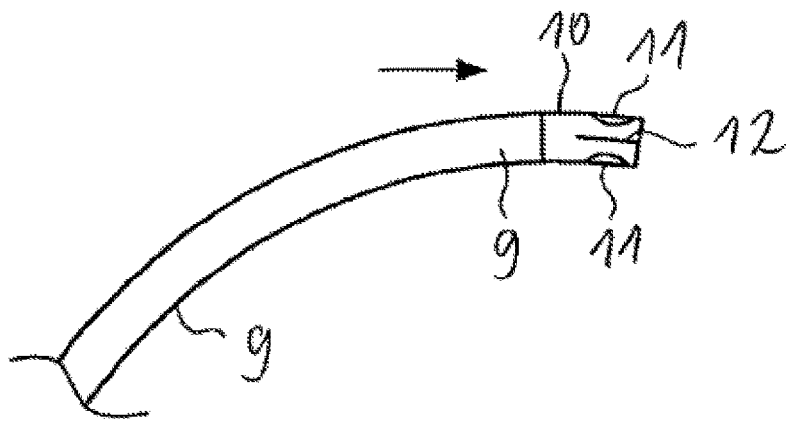
Figure 9:
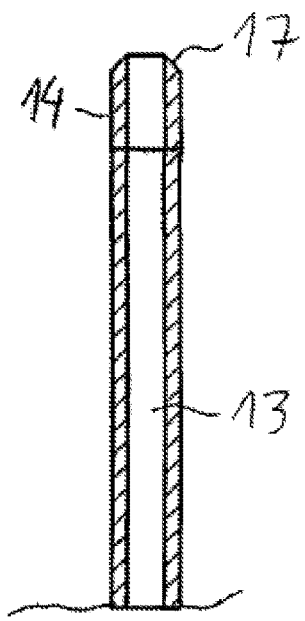
Figure 10:
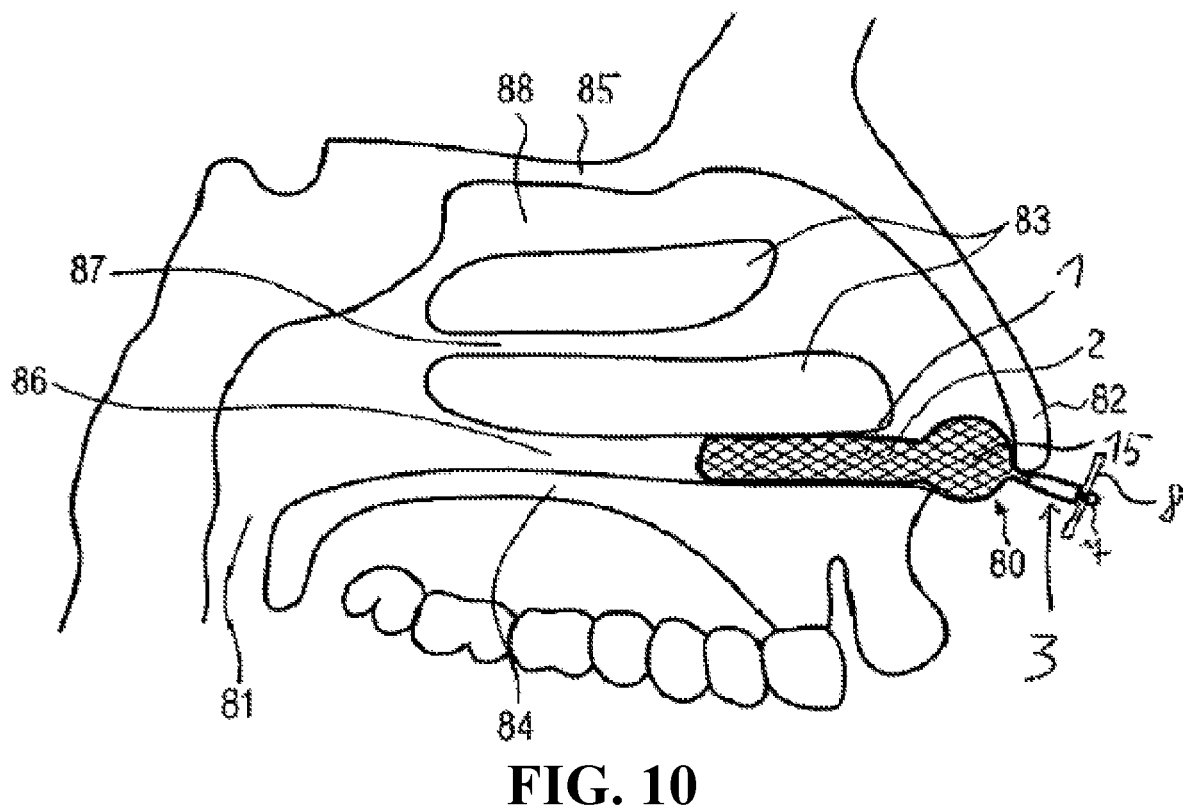
Figure 11:
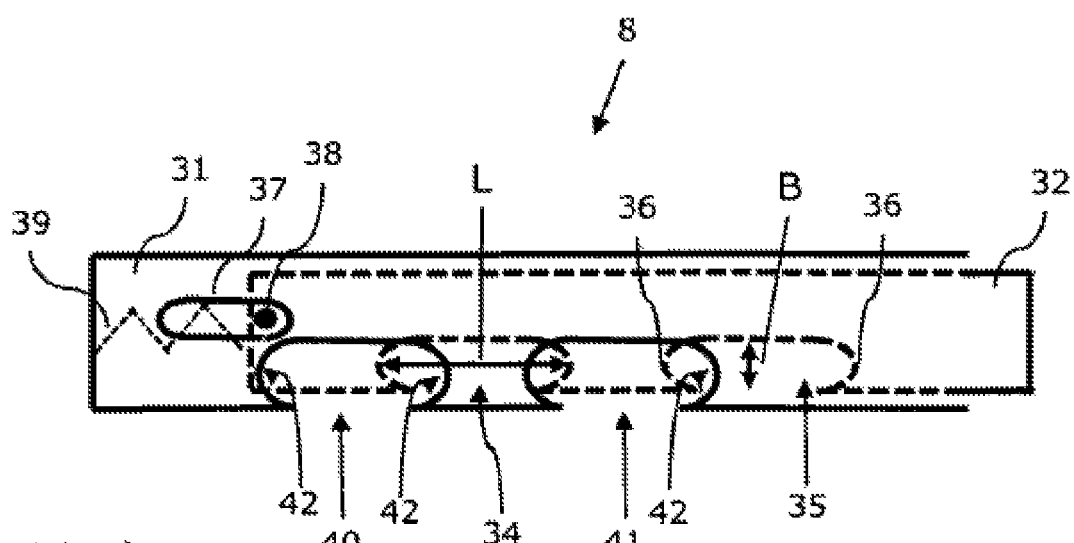
Figure 11:
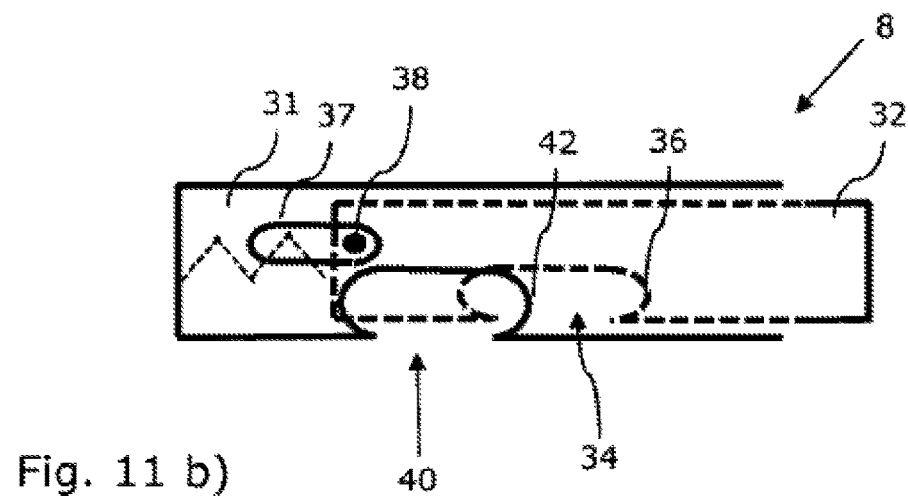
Figure 12:
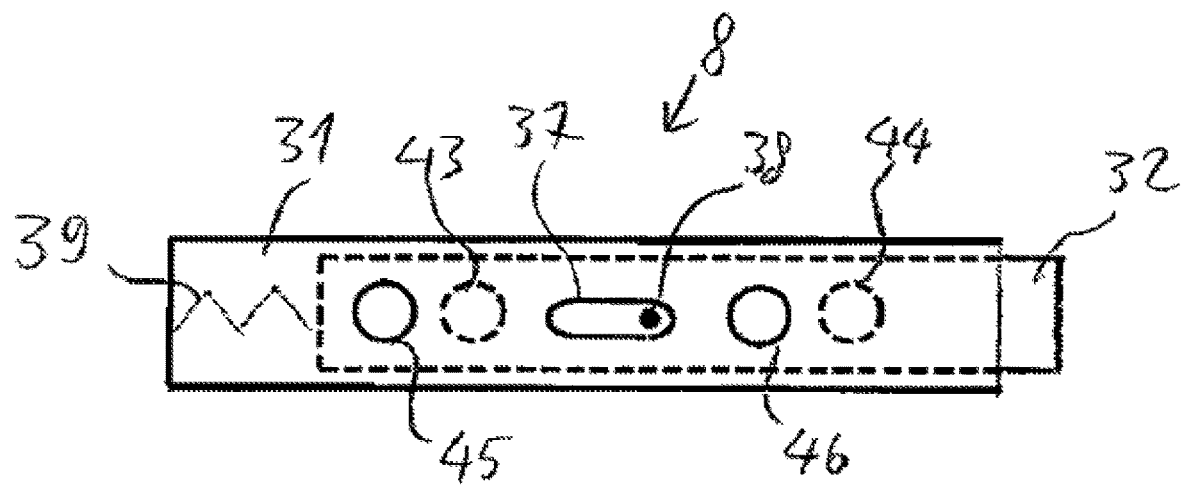
Figure 12:
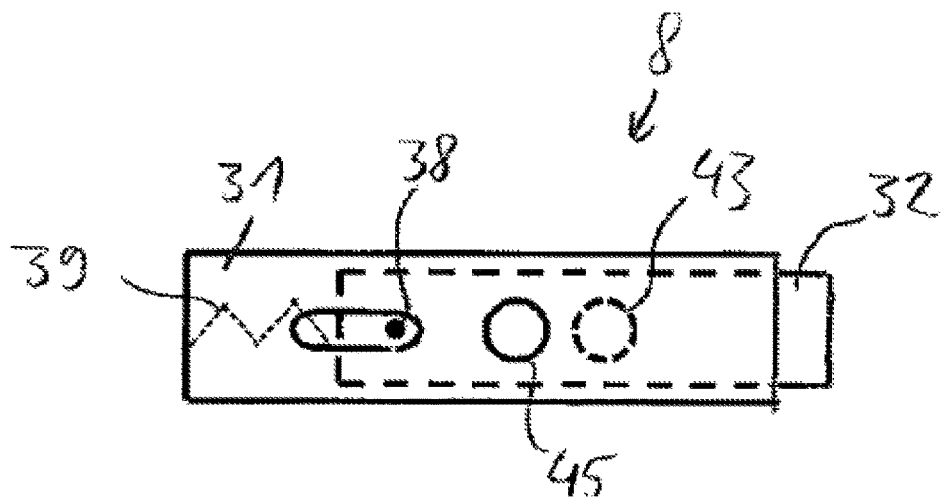
Figure 13:
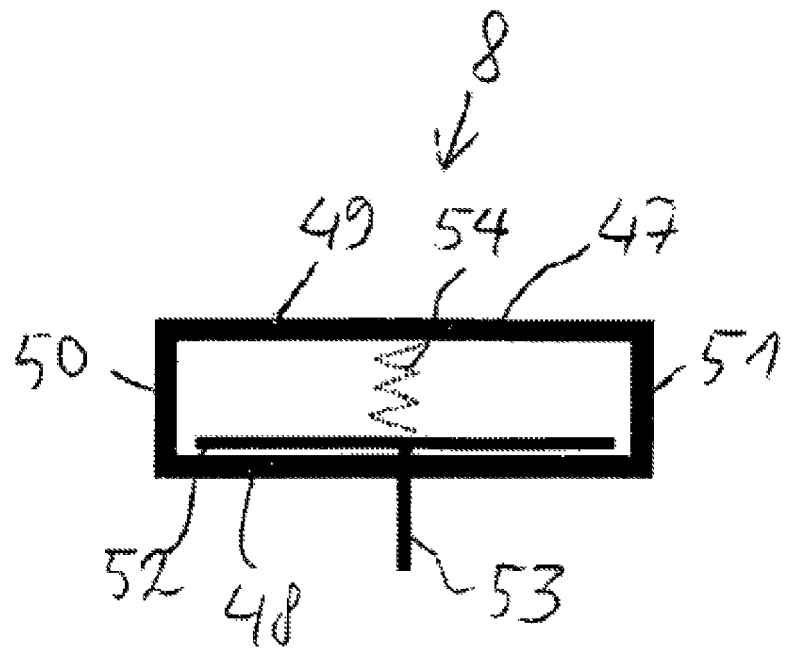
Figure 13:
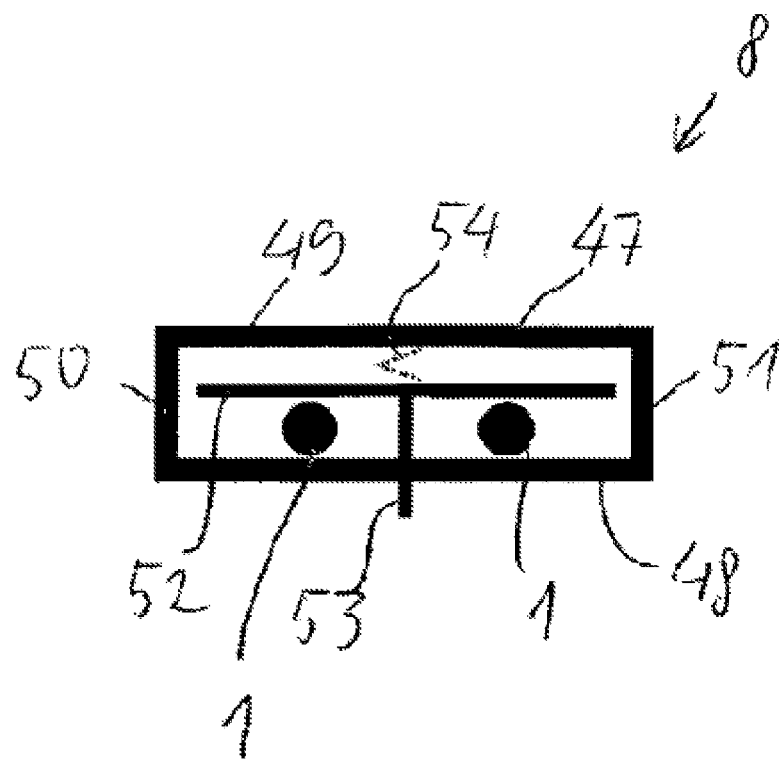
Figure 14A:
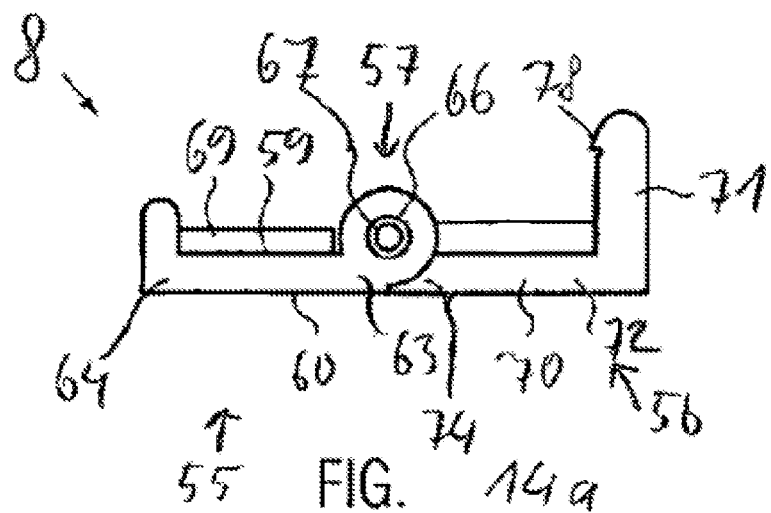
Figure 14B:
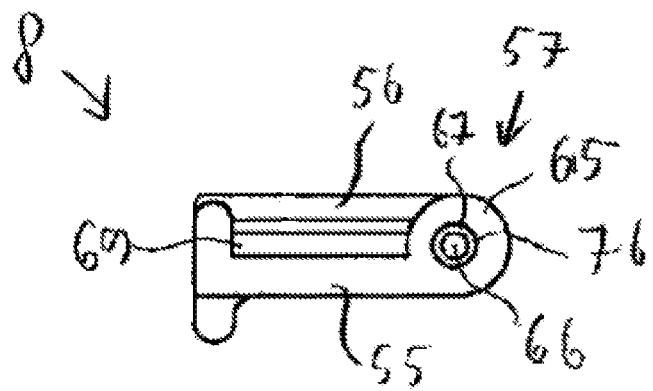
Figure 14C:
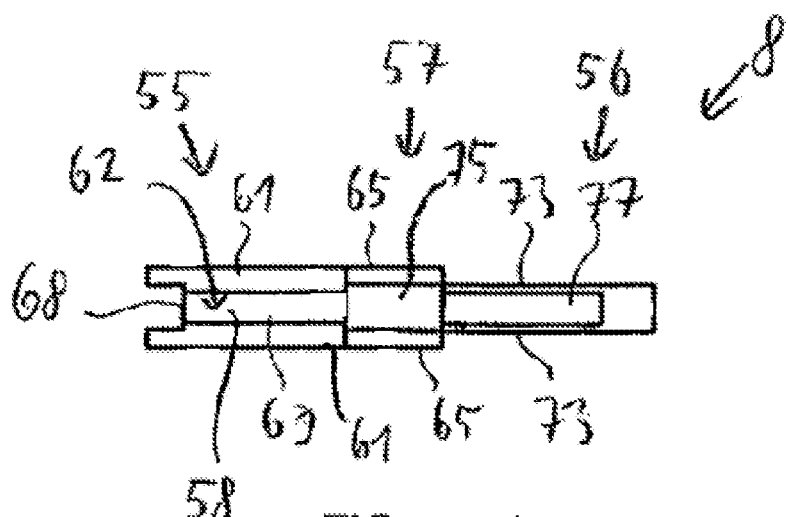
Figures 15A, 15B:
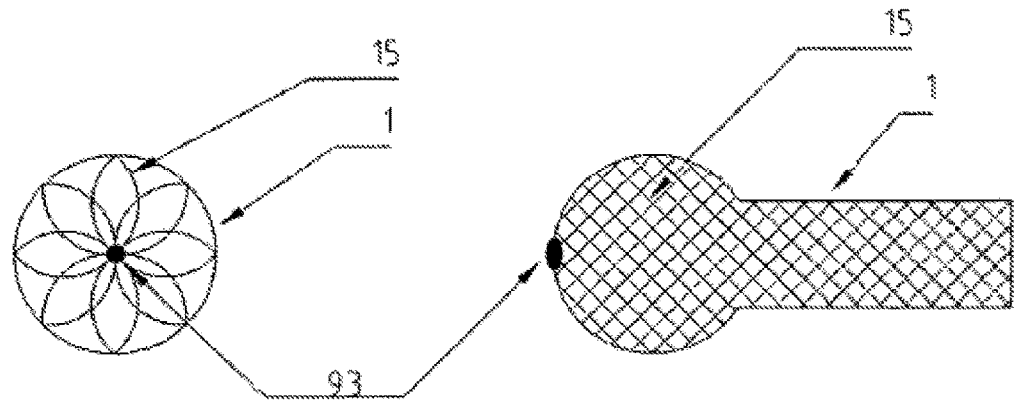
Figures 16A, 16B:
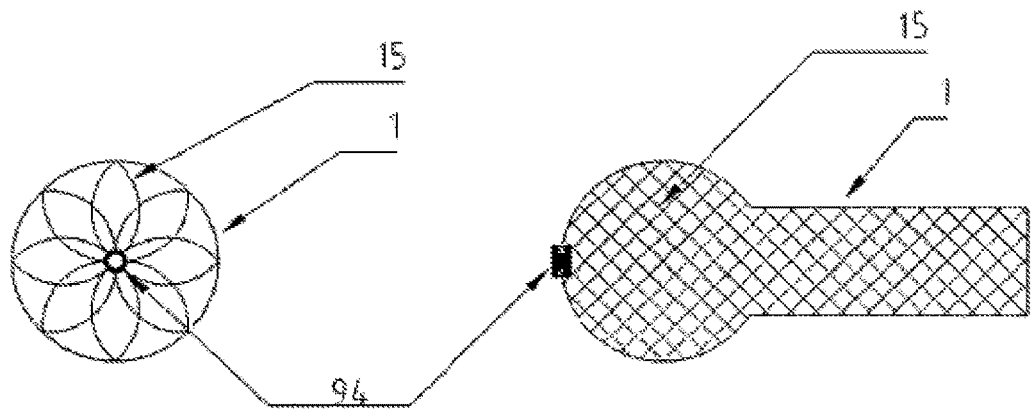
Figures 17A, 17B:
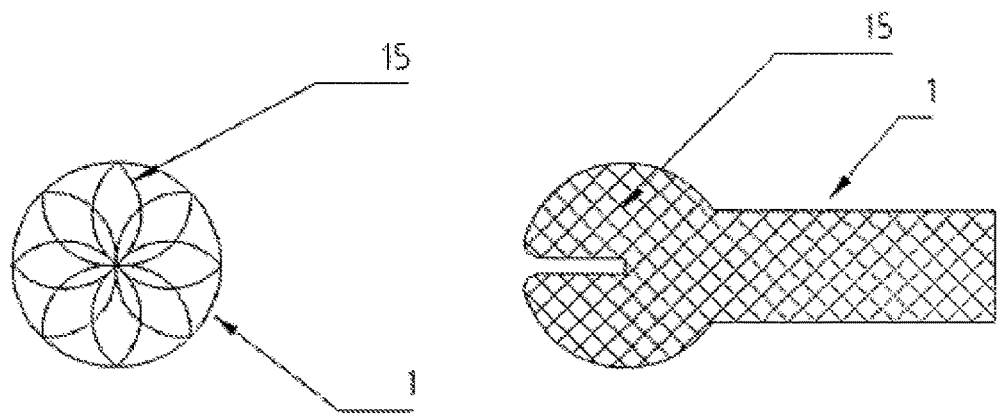
Figures 18A, 18B:
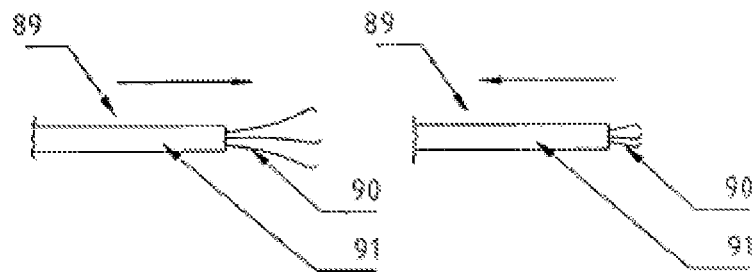

The invention will now be exemplified in more detail on the basis of the embodiments illustrated in the drawings in which:

FIG. 1 shows a stent according to a first embodiment of the invention in a schematic side view, FIG. 2 shows a stent according to a second embodiment of the invention in a schematic side view, FIG. 3A shows a stent according to a third embodiment of the invention in a schematic side view, and FIG. 3B shows a stent identical to that of FIG. 3A except for having fixation section 3 conically tapered as in the stent of FIG. 1, FIG. 4 shows a stent according to a fourth embodiment of the invention in a schematic side view, FIGS. 5*a*, 5*b* show each a holding element in a top view, FIG. 6 shows another holding element in a top view, FIGS. 7*a*, 7*b* show a holding element in a top view and a side view, FIG. 8 shows a section of an inserting rod in a side view, FIG. 9 shows a section of an introduction tube in a section view, FIG. 10 schematically shows the nasal cavity in a section view, FIGS. 11*a*, 11*b* schematically show another holding element in a side view grossly simplified, FIGS. 12*a*, 12*b* schematically show another holding element in a side view grossly simplified, FIGS. 13*a*, 13*b* schematically show another holding element in a side view grossly simplified, FIGS. 14*a*-14*c* schematically show another holding element in a side view grossly simplified, FIGS. 15a,b-17a,b each show a proximal ending region of a stent without a fixation section in a front view (FIG. a) and in a side view (FIG. b), and FIGS. 18a, 18b, 19a, 19b, 19c, 20a, 20b, 20c each show a removal tool for removal of a stent from a nose in different grasping conditions.

Figure 21:
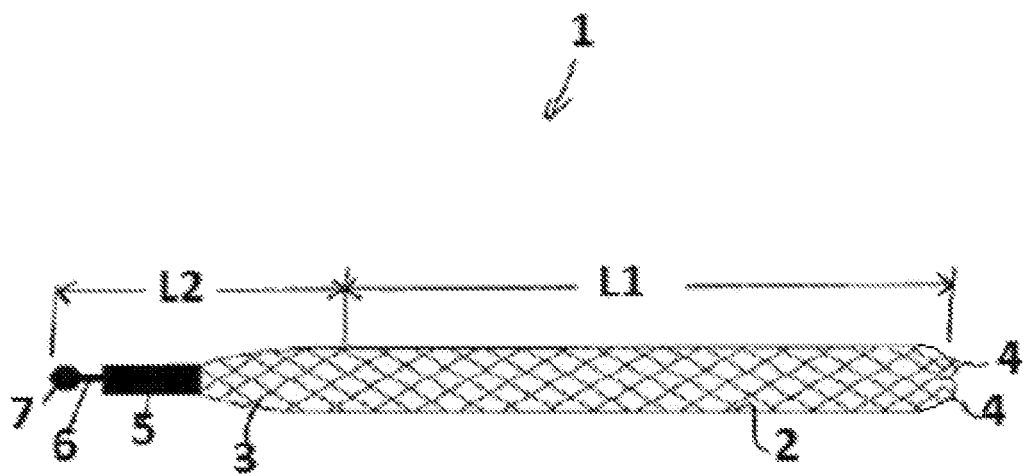

FIG. 21 shows a stent according to an embodiment of the invention in a schematic side view wherein the distal end of the support body is provided slightly tapered relative to the other part of the support body.

A stent 1 according the invention for splinting of a nasal passage comprises a support body 2 and a fixation section 3.

FIG. 1 shows a first embodiment of a stent 1 wherein the support body 2 is provided tubular with a constant diameter and the fixation section 3 conically tapers from the distal to the proximal end. The support body 2 as well as the fixation section 3 are integrally made from one wire braid. Each individual wire directed towards the distal end of the stent 1 is returned at the distal end of the support body 2 towards the proximal end of the stent 1. The bends resulting from that are referred to below as round ends 4. These have in unloaded state of the stent a diameter in the range of 0.5 to 2 mm. Thereby a distal end is provided without any individual free wire ends. No free wire ends need to be connected with another element. The round ends prevent injury of the airways caused by the distal end of the stents.

The stent 1 can be braided with a single wire or with a multitude of wires. The ends of the wire or the wires, respectively, are connected at the proximal end of the stent or at the proximal end of the fixation section 3, respectively, with a pencil-shaped or a cylindrical body 5. In the present embodiment the pencil-shaped body 5 is a body 5 crimped around the ends of the wires. Therefore it can also be referred to as a crimping body 5. At the distal end of the crimping body 5 a thin pin 6 is provided. At the end of the pin 6 distant from the crimping body 5 a ball clutch 7 is provided. With the ball clutch 7 the stent can be connected to another element which provides a respective mating coupling element.

The stent is braided from an elastic wire with a diameter of 0.001 mm to 2 mm, particularly with a diameter of 0.05 mm to 0.5 mm and preferably with a diameter of 0.07 mm to 0.2 mm. The wire particularly is a metal wire and preferably a nitinol or steel wire.

The length L1 of the support body 2 is 25 mm to 120 mm and particularly 25 mm to 100 mm. Preferably the length L1 of the support body is in the range of 30 mm to 50 mm or 60 mm to 120 mm, or, respectively, 30 mm to 50 mm or 70 mm to 100 mm. For the longer embodiment a range of 70 to 100 mm is most preferred.

The diameter of the support body 2 is in the range or 4 mm to 20 mm. Preferably the support body has a diameter of at least 5 mm and particularly of at least 6 mm.

The fixation section 3 has a length L2 of about 10 to 25 mm. With the fixation section the stent can be fixed at the body of the user so that the stent cannot move from the nasal passage of the user towards the throat. For that purpose it is necessary that the fixation section extends through the nostril towards the outside in order to be fixed there with the respective fixation element. Such a fixation element e.g. can be a plaster with which the fixation section 3 is taped in the region below the nose of the user. Yet, a holding element 8 if preferred which extends at least in one direction that far that it cannot be introduced through a nostril into a nasal passage. Alternatively, the holding element 8 can be provided in such a way that it can be connected to two stents 1 so that it extends as a holder between the two stents and prevents pulling in too far of the stent into the nasal passage. Such a holding element 8 which is described in more detail in the following preferably is connected to the coupling element of the stent which—in the present embodiment—is provided as a ball clutch 7. Within the scope of this invention, however, it is also possible to provide the holding element as a clamp which is clamped to the fixation section 3 of a stent 1 or to the fixation sections 3 of two stents 1.

An insertion rod 9 which can be coupled to the coupling element 7 is shown in FIG. 8. The inserting rod 9 is made from plastic. At the distal end of the inserting rod 9 as a single-piece a tubular bushing or sleeve 10 is provided. The bushing has two diametrically opposite circular openings 11. In longitudinal direction of the inserting rod 9 in the area of the two circular openings 11 a slit 12 may be provided. The slit 12 extends to the distal end of the bushing 10. The bushing 10 may be integrally formed at the distal end of the inserting rod 9 or be provided separately, made from another material, and be force-fitted connected to the inserting rod 9, e.g. by gluing. The ball clutch 7 of the stent 1 can be fitted between the two openings 11 of the bushing 10 of the inserting rod 9. In this way a detachable connection of the stent 1 and the inserting rod 9 is provided. The longitudinal slit 12 provided in the bushing 10 simplifies introduction and removal of the ball clutch 7 into or from, respectively, the bushing 10. The relation between the diameter of the ball clutch 7 to the inner diameter of the bushing 10 and the hardness of the material of the bushing 10 and the length of the slit 12 can be used for adjustment of the connecting or holding force of the connection between the ball clutch 7 and the bushing 10. The ball clutch 7 is freely rotatable in the bushing 10.

The inserting rod also can be provided as an inserting tube (not shown) in which at one end the two circular openings and optionally a slit—similar to the bushing 10—can be integrated. Thereby the need for separate manufacturing of the tubular bushing is obviated.

The diameter of the inserting rod 9 and of the crimping body 5 are such dimensioned that the inserting rod 9 together with the stent 1 can be introduced into an insertion tube 13 (FIG. 9). The introduction tube 13 is made from a suitable and sufficiently hard polymer, e.g. PEBAX with a shore hardness of 50 Shore D to 80 Shore D, e.g. PEBAX 7233 (Shore hardness 69D), PEBAX 6333 (Shore hardness 64D) or PEBAX 55 (Shore hardness 54D). At the distal end of the insertion tube 13 an introduction tip 14 may be provided as a single-piece. The introduction tip has the same inner as well as outer diameter as the introduction tube 13 and is provided flush-mounted with this. The introduction tip 14 can be made from a flexible, significantly smoother material, e.g. PEBAX with a Shore hardness of 25 Shore D to 45 Shore D. Such a single-piece introduction tube can be made from a single material, e.g. PEBAX 7233, PEBAX 6633 or PEBAX 5533. It is possible to manufacture such a single-piece introduction tube in an extrusion process with a continuous material gradient. Such an insertion tube has a transition section in which the share of the one material decreases and correspondingly the share of the other material increases. Material for such a tube e.g. are PEBAX 7233 in the section of the main body and PEBAX 3533 in the region of the insertion tip 14 so that the insertion tip is smoother than the main body. Regarding the selection of the materials the above description for the two-piece introduction tube apply appropriately.

The introduction tube also can be provided with multiple layers whereas the inner layer preferably is harder than the outer layer in order to provide a more slippery inner surface with low friction (e.g. PEBAX 7233). Thereby, the stent can be introduced and retracted with low drag into the introduction tube. The outer layer preferably has a Shore hardness of e.g. 60A to 95A and is thicker than the inner layer for that the introduction tube generally has smooth and flexible materials properties and therefore easily adapts to the course of the nasal passage. In that way the tube can be easily introduced. Preferably the outer layer is made from PU 85A with a thickness of about 0.2 mm and the inner layer from PEBAX 7233 with a thickness of about 0.1 mm. Melting of a short tip from PU 85A (about 2 to 10 mm long) which preferably is atraumatically rounded further increases comfort and safety during introduction of the tube through the nasal passage. The introduction tube 13 may be shape straight. It may also have a curvature.

The outer diameter of the introduction tube is up to 10 mm, preferably up to 5 mm, in order to enable for the user a comfortable introduction of the tube without pain. The inner diameter of the introduction tube is up to 4 mm in order to provide sufficient lumen for uptake of the stent 1.

The introduction tip provides a chamfer 17 at the outer edge. Instead of the chamfer 17 the introduction tip 14 also can be provided with a rounding. Such a rounding e.g. can be produced by thermal reshaping or by means of abrasion or laser ablation. Such a rounding can be provided inside and/or outside.

Such a rounded tip is more laborious in manufacturing than a chamfer. The rounded tip, however, is even more secure during insertion of the stent. Further, the thin-walled end resulting form chamfering may harden by release of plasticizers from the polymer due to the relatively large surface.

The introduction tube may also have an olive or drop shaped thickening at one end or both ends in order to facilitate introduction into the nasal passage. The olive of the drop at the end of the introduction tube has a length of 2-20 mm, preferably 2-10 mm and even more preferred 2-5 mm. The diameter of the olive or the drop is about 3.5-6.0 mm, preferably 4.0-5.0 mm.

These shaped introduction tips 14 are atraumatic tips whereas the shape should be even more smooth and round the harder the material of the tip is. An olive or drop shaped embodiment has a greater frontal area and therefore exhibits the best pressure distribution towards the nasal tissue.

For introduction of the stent 1 into the introduction tube 13 the stent 1 first by means of the ball clutch 7 is fixed at the bushing 10 of the inserting rod 9. The inserting rod then is inserted with its proximal end into the introduction tip 14 of the introduction tube 13. The insertion rod 9 is pushed through the introduction tube 13 until the stent 1 is completely inserted into the introduction tube 13. The stent 1 may minimally protrude from the introduction tube. It is essential that the stent 1 is compressed by introduction into the introduction tube 13 to a smaller diameter so that it can be easily introduced into the nasal passage together with the introduction tube and the inserting rod. Alternatively the stent 1 is pushed into the introduction tube 13 without a coupling element 7 and no detachable connection with an inserting rod is prepared. Embodiments without coupling elements are described in more detail further below.

When this assembly of stent 1, introduction tube 13 and inserting rod 9 is advanced that far that the support body is positioned in the nasal passage, first the introduction tube 13 is retracted over the inserting rod 9 and then the inserting rod is detached from stent 1. The smooth surface of the introduction tube 13 significantly simplifies introduction of the stent 1 into the nasal passage.

FIG. 2 shows a second embodiment of the stent 1 which is provided similar to the first embodiment. Therefore same parts have same reference numbers and are not described a second time. The stent 1 according to the second embodiment differs from stent 1 of the first embodiment solely in that the fixation section 3 does not conically increase but is provided about parabolically tapered whereas it tapers more strongly with increasing neighborhood to the crimping body 5.

FIG. 3A shows another embodiment of the stent 1 whereas again same parts as in the previous embodiment have the same reference numbers. This stent 1 differs from the above embodiments in that the proximal ending region of the support body 2 has a widened section 15. The widened section 15 in the present embodiment is about ball-shaped widened. The shape of the ball-shaped widened section may slightly differ from an ideal ball-shape, e.g. be oval. It is essential that the widened section does not form any edges which press against the nasal alars but that due to its rounded shape it smoothly supports from the inside the respective nasal alar. The ball-shaped widened section should have a diameter of at least 10 mm, preferably 12 mm and particularly 13 mm in order to obtain an efficient widening of the nasal alars. The diameter, however, should not be too large so that no strong pressure is exerted onto the nasal alars. A maximal diameter of 20 mm, therefore, particularly of 17 mm or 15 mm, respectively, is useful. The remaining support body 2 consequently is provided shorter by the length of this section when compared to the above described embodiments so that the overall length remains about the same.

This ball-shaped widened section 15 is provided in order to be positioned in the region directly behind the nasal entry so that the nasal alars can be splinted to prevent a collapse.

FIG. 3B shows a stent identical to that of FIG. 3A except for having fixation section 3 conically tapered as in the stent of FIG. 1.

Particularly for the embodiments comprising a widened section it may be advisable not to include a fixation section because the ball-shaped widened section 15 already provides a sufficient fixation in the nose so that a holding element is not absolutely necessary.

In the following some embodiments of the stent without a fixation section or without a coupling element, respectively, are described on the basis of FIGS. 15, 15b to 17a, 17b.

In the embodiment according to FIG. 15a, 15b the widened section 15 is provided in a way so that the wire ends are connected in a polymer drop 93. The polymer drop preferably is applied to the free wire ends as a liquid polymer or liquid glue and maintained in shape as long as the polymer is fully hardened. After hardening the wire ends are fixed and neither the braid nor the body tissue getting into contact therewith can be damaged by sharp-edged tips.

In a further embodiment (FIGS. 16a, 16b) the wire ends are connected by a single- or two-piece ring 94 similar to a rivet. For that the wire ends are inserted into a circumferential slit at this ring and subsequently this slit is compressed or crimped.

According to another embodiment (FIG. 17a, 17b) the wires are connected by braiding or heat treatment whereas the wire ends are returned into the inner lumen of the ball-shaped widened section. For that the proximal end of the braid may be equipped with twists so that distortion and fringing can be excluded. Additionally the wire ends may be e.g. crimped with a sleeve and thereby fixed.

In case of a stent without a coupling element the introduction tube is retracted over an inserting rod which does not comprise a tubular bushing or over an inserting tube which does not have openings nor a slit whereby the stent self-expands and positions itself in the nasal passage.

In FIGS. 3A and 3B the wire braid is represented only schematically. Such a shape e.g. can be achieved by braiding of a cylindric stent from a nitinol wire whereby the cylindric stent is positioned on a tool which represents the shape of the support body 2 and provides a ball-shaped section and a cylindric section. By a special heat treatment which is known by skilled persons as annealing then the shape of the molded body in the braid is impressed in the nitinol wire braid. After removal of the molded body the stent remains in this shape.

FIG. 4 shows another embodiment of the stent 1 whereas again same parts as in the previous embodiment have the same reference numbers. This stent differs from the three other above described embodiments in that the fixation section 3 is not braided but that the wires run either individually about in parallel from the support body 2 to the pencil-shaped body or crimping body 5, respectively, or the wires are twisted and the twisted strands 16 run about in parallel from the support body 2 to the pencil-shaped body. In that case each two, three or four wires may be twisted into a twisted strand 16. The advantage of this fixation section 3 relies in its very high flexibility and that the stent is highly bendable in the region of the fixation section 3. This fixation section 3 of course may also be combined with the widened section 15 according to the third embodiment.

In case the stent 1 is provided without a coupling element (e.g. a ball clutch) then it is useful to provide a removal tool for removal of the stent 1 from the nose. The most simple version is a thin elongated plastic or metal body which is uncinated at its distal end (not shown). This curvature is inserted into the wire braid of stent 1 and the stent is retracted from the nose with the removal tool.

Alternatively, different other embodiments of removal tools 89 as described in the following on the basis of FIGS. 18a to 20c can be applied.

A second embodiment of a removal tool 89 (FIGS. 18a, 18b) exhibit elastic tentacles 90 similar to the chuck of a drop-action pencil which are slidably mounted in a sleeve 91. When pushing the tentacles 90 out of the sleeve 91 their free ends expand due to their spring effect. The tentacles 90 have inwardly facing hooked edges. With these hooked edges they are inserted into the braid of stent 1. Once the tentacles are positioned in the braid the tentacles 90 are pulled into the sleeve 91 to the extent that the stent 1 is securely fixed. Then the stent is pulled out of the nose.

Figures 19A, 19B, 19C:
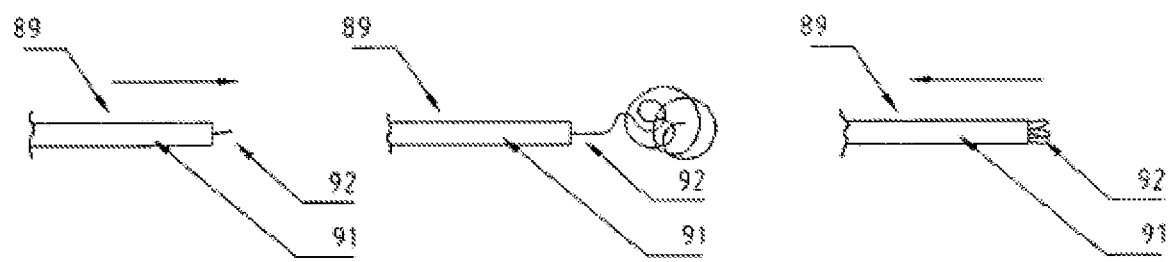
Figures 20A, 20B, 20C:
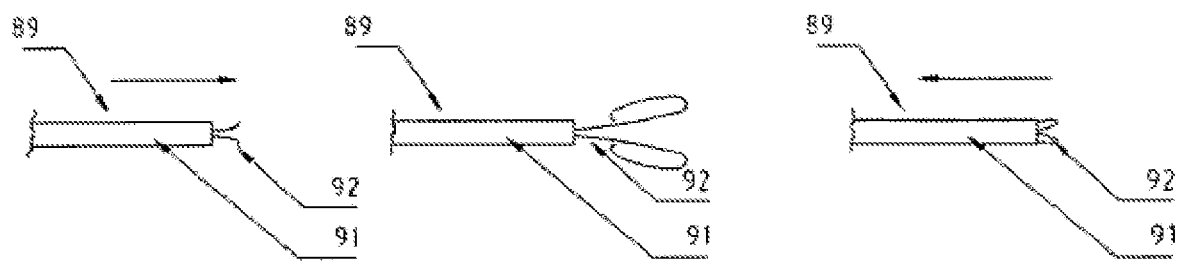

In FIGS. 19a to 19c a third embodiment of the removal tool 89 is shown which again provides a sleeve 91. In the sleeve 91 a slidable trap wire 92 is positioned. The trap wire 92 is elongated when inside the sleeve because the inner diameter of the sleeve 91 is only slightly larger than the diameter of the trap wire 92. The trap wire 92 is pre-shaped such that it self-coils when released from the sleeve 91 and forms a knot. For fixing at the sleeve the removal tool 89 is positioned at the proximal end of the stent with the trap wire 92 pulled into it. Subsequently the trap wire 92 is pushed out off the sleeve 91. The trap wire 92 forms the knot inside the braid of the stent 1 whereby a sufficient tensile force is exerted to pull out the stent off the nose. In this way the stent 1 is removed from the nose.

A fourth embodiment of a removal tool 89 (FIGS. 20a to 20c) is provided similar to the third embodiment of the removal tool shown in FIGS. 19a to 19c. The fourth embodiment of the removal tool 89 comprises again a sleeve 91 whereas several trap wires 92 which each are pre-shaped in a loop-like manner are positioned therein. For grasping the stent the removal tool 89 is positioned with the orifice of the sleeve 91 at the proximal end of the stent. Subsequently the trap wires 92 are pushed out off the sleeve 91. The trap wires self-expand inside of the braid of stent 1 so that the stent can be pulled out off the nose.

In the following some holding elements are described:

FIG. 5a shows a first embodiment of a holding element 8 that in the top view is formed by an about rectangular plastic plate. The edges of the plate are rounded. The plate has a length of about 3-4 cm and a width of about 0.7-1.5 cm. In the center of this plate-like holding element 8 a circular opening 18 is provided with its diameter being slightly larger than the diameter of the ball clutch 7 of the stent 1. From this opening 18 two slits 19 extend in parallel to the longitudinal edge 20 of the plate-like holding element 8. The slits 19 are positioned in about the middle between the opposite longitudinal edges 20. The slits have a width which is smaller than the diameter of the ball clutch 7. Preferably the slits are provided as incisions without any distance between the opposite edges of the incision.

A ball clutch 7 of a stent 1 can be passed through the opening 18 of the holding element 8 and the stent can be moved along one of the two slits 19 whereby the stent 1 extends with its pin 6 or with the wire braid through the respective slit 19. A second stent can be inserted with its ball clutch 7 into the opening 18 and be moved into the other slit 19. The stents 1 are mounted in the holding element 8 once they are already introduced into the nasal passage and the introduction tube and the inserting rod have been removed. Due to the positioning of the stents 1 in the nose they are located remote from each other so that a movement of the ball clutches 7 towards the openings 18 is securely prevented. Thereby the holding element is captively connected to both stents 1. The holding element 8 thus creates a holder between the two stents 1 which prevents movement of the stents too far down into the nasal passages and especially into the throat.

Is is also useful to provide the opening 18 with a funnel (not shown) at the holding element 8 which simplifies insertion of the ball clutch 7. During insertion of the ball clutch 7 into the opening 1 the stent 1 is positioned with its support body in the nasal passage. Thereby the ball clutch 7 is located directly at the nose and at the border of the field of vision of the user. Therefore, such a funnel is highly beneficial as in this way it is possible to connect the holding element to the stent 1 without a need to see the holding element and the fixation section 3 of the stent 1.

FIG. 5b shows a second embodiment of a holding element which is provided similar to the first embodiment in FIG. 5a. Therefore same parts have same reference numbers and are not described a second time. This holding element again is provided as a rectangular plate with two longitudinal edges 20. It provides again two slits 19. The two slits 19 each end in a separate opening 21, 22 which are a little displaced away from the center of the plate.

A third embodiment of a holding element 8 is shown in FIG. 6. This holding element is provided similar to the holding element shown in FIG. 5a. Therefore same parts have same reference numbers and are not described a second time. At the front sides orthogonal to the longitudinal edges of the rectangular plate each a support wing 23 is provided. The support wing in the top view is a rectangular plate which extends with its longitudinal edges 24 angular to the longitudinal edges 20 of the main body of the holding element 8. The two support wings 23 each are angled to the same side relative to the slits 19. The support wings can be fixed below the nasal alars after fixation of the stent 1 with the holding element 8 so that they keep open the nasal alars. This holding element primarily can be combined with the stents according to the embodiments which do not provide a widened section for keeping open the nasal alars according to FIGS. 1, 2 and 3.

The longitudinal edges 24 of the support wings 23 with their longitudinal edges 20 form the boundaries of the main body of the holding element 8 with an angle in the range of 120° to 150°.

FIGS. 7a and 7b show another embodiment of a holding element 8. This holding element again is provided plate-like and in the top view rectangular with two longitudinal edges 20. This plate comprises a stiff enclosure 25 which in the top view is provided about bone-shaped with two circular sections 26 and a connecting strut 27 between the circular sections 26. This stiff enclosure 25 is made e.g. from spring steel. The other part of the plate-like holding element 8 is made from a flexible plastic material, particularly an elastomer. In the region of the longitudinal center of the stiff enclosure which in FIG. 7a is labelled with the reference number 28 the stiff enclosure 25 integrally is connected with the other plastic material why this region is referred to below as the connecting region 28. Flanking the connecting region 28 the stiff enclosure 25 is fully stamped out of the flexible plastic material as shown in FIG. 7a with two stamping lines. The flexible plastic material thereby forms two flexible latches 30 which are connected to the stiff enclosure 25 at the connecting region 28. The flexible latches 30 thus exhibit openings whose shape is complementary to the end regions of the stiff enclosure 25.

As schematically shown in FIG. 7b the flexible latches 30 can be lifted from the end region of the stiff enclosure 25 so that the openings present in the latches 30 can be uncovered. Each one fixation section 3 of the stent 1 can be passed through an opening. The fixation section 3 then is clamped between the end sections of the stiff enclosure 25 and the flexible latch 30 and thereby captively connected to the holding element 8.

This holding element 8 according to FIGS. 7a and 7b is simply constructed and cheaply producible.

Nevertheless it provides for a secure clamping of the fixation sections 3 of two stents 1. In the context of the invention it is of course possible to also use other clamping elements, particularly clips with a spring element which impinge on two clamp jaws. Further, the holding element 8 can be provided with one or two bushings which are designed such as the bushing 10 of the inserting rod 9. These bushings also enable a coupling of the stent(s) to the holding element.

The holding elements according to FIG. 5b, FIG. 6 and FIGS. 7a and 7b additionally may have an integral funnel in the region of their openings 18, 21, 22, 29.

FIG. 11a shows another holding element 8 which consists of a tubular elongated hollow sleeve or housing 31 and an insert 32 which is slidably mounted in the housing 31. The housing 31 has one end closed by a front wall 33 and one open end. The insert 32 is adapted to the shape of the housing 31 wherein the housing 31 and the insert 32 preferably have a rectangular, particularly square, or a circular cross section. The insert 32 can be a solid plastic body with a first recess 34 and a second recess 35 at one longitudinal edge. The recesses 34, 35 extend from the longitudinal edge with a preset depth B into the insert 32. In longitudinal direction the recesses 34, 35 extend in a preset length L which preferably is significantly greater than the depth B. Each end of the recesses 34, 35 in longitudinal direction has a concave curvature shape 36.

The housing 31 provides two diametrically opposite longitudinal slits 37 in which each one end of a transverse pin 38 which is connected to the insert 32 is positioned. The transverse pin 38 limits the movement of the insert 32 in the housing 31 wherein in a maximally pushed in position of the insert 32 the transverse pin 38 touches the longitudinal slit 37 at its end directing towards the front wall 33. In a maximally delivered position of the insert 32 the transverse pin 38 touches the longitudinal slit 37 at its end distal to the front wall 33. The length of the longitudinal slit 37 therewith corresponds to the maximal way of the insert 32 in the housing 31. Between the front wall 33 and the insert 32 is placed a spring element 39 which pushes the insert 32 into the maximally delivered position (FIG. 11A).

The housing 31 provides also a first recess 40 and a second recess 41 which have about the same shape as the first recess 34 and the second recess 35 of the insert 32 and align in the maximally pushed-in position of the insert 32 with the recesses 34, 35. The recesses 40, 41 therefore also have concave curvatures 42 which limit the recesses in their longitudinal direction.

In the pushed-in position of the insert 32 in which the first recesses 34, 40 and the second recesses 35, 41 approximately align thus an about continuous recess results in which each one fixation section 3 of a stent 1 can be inserted. When the insert 32 is released it is pushed away from the front wall 33 by the spring element 39. The concave curvatures 36 of the recesses of the insert and the concave curvatures 42 of the housing 31 move towards each other and clamp the fixation sections 3 of the stents 1.

The insert 32 is activated at its section protruding from the open end of the housing 31 and is pressed against the spring element 39.

FIG. 11b shows another holding element 8 which is provided similar to the holding element 8 according to FIG. 11a but has only one single recess 34 in the insert 32 and a single recess 40 in the housing 31 which align when the insert 32 is pushed-in. With this holding element a single stent can be fixed. Two such holding elements can be connected with a flexible strip so that with each of the holding elements 8 one stent 1 can be fixed. The use of two holding elements 8 interconnected with a flexible strip has the advantage that first one of the two holding elements is coupled to one of the stents and subsequently the other one independent of the other holding element can be adjusted towards the second stent and coupled to this.

FIG. 12a shows another holding element 8 which is provided similar to the holding element shown in FIG. 11a. Therefore same parts have same reference numbers and are not described a second time. The holding element according to FIG. 12a differs from that according to FIG. 11a solely by the provision of openings 43, 44 in the insert 32 and openings 45, 46 in the housing 31 which align when the insert is pushed-in. In the present embodiment the openings 43 to 46 are circularly shaped. In the context of this invention it is of course possible to provide the longitudinal openings instead of the circular openings which are aligned in longitudinal direction of the housing 31 and the insert 32, respectively In FIG. 12b a holding element 8 is shown which is similar to the holding element according to FIG. 12a whereas this holding element has each an opening 43, 45 in the insert 32 and the housing 31 which align when the insert 31 is pushed-in. The holding element 8 according to FIG. 11b serves for fixation of a single stent. Two of these holding elements can be connected by a flexible strip for fixation of two stents.

FIG. 13a schematically grossly simplified shows a further holding element 8 which provides a rectangular frame 47 with two longitudinal struts 48, 49 and two transverse struts 50, 51. In this frame 47 a stamp plate 52 is provided which is centrically connected with a guiding rod 53 which is arranged orthogonally to the stamp plate 52. On the side averted from the guiding rod 53 a spring element 54 is provided between the stamp plate and the longitudinal strut 49. This spring element presses the stamp plate against the longitudinal strut 48. The guiding rod 53 extends through a respective hole in the longitudinal strut 48 so that the stamp plate 52 is guided in parallel to the longitudinal struts 48, 49.

For connection of this holding element 8 with the fixation sections 3 of two stents 1 the guiding rod is pushed-in against the action of the spring element 52 into the frame 47. In this region between the stamp plate 52 and the longitudinal strut 48 then both fixation sections 3 of the stents 1 can be inserted. Upon release of the guiding rod 53 the stamp plate 52 is pressed against the longitudinal strut 48 why the fixation sections 3 of the stents 1 are clamped between the stamp plate 52 and the longitudinal struts 48.

The advantage of this holding element 8 resides in that the opened area between the stamp plate 52 and the longitudinal struts 48 is quite large so that it is easy to insert the fixation sections 3. In PCT/EP 2010/004687 a fixation device is disclosed which may be used here, too, as a holding element 8 (FIGS. 14a to 14c). Reference is therefore made to this document.

This holding element 8 comprises a first and a second clamp jaw 55, 56 which are interconnected by a joint 57.

The first clamp jaw 55 in the following is referred to below as the base jaw. The base jaw 55 provides a base wall 58. The base wall comprises a top side 59, a bottom side 60 and two side walls 61 extend from the base wall 58 an their longitudinal sides upwards so that the base wall 58 and the two side walls 61 confine a U-shaped recess. The two opposite ends of the cuboidal base wall 58 are referred to as the joint side 63 and the lock side 64.

Two annular disk members 65 are formed at a distance from each other on the joint side 63 of the base wall 58. They are flush with the outer surfaces of the side walls 61. The annular disk members 65 have a circular opening 66 each which are aligned to each other. The openings 66 are designed to receive a tubular shaft 67 each. The tubular shaft is rotatably arranged in the openings 66 and aligned with the outer surfaces of the side walls. The first clamp jaw 55 is pivotably connected to the second clamp jaw 56 via the tubular shaft 67.

The side walls 61 extend at the locking side 64 beyond the front-end edge of the base wall 58 and therefore they define the U-shaped recess in a top view of the base jaw 55. The side walls are somewhat higher in this area.

The front-end edge of the base wall 58 on the bottom side 60 is referred to below as the locking edge 68.

A cuboidal fixing block 69 is arranged in the U-shaped recess or the groove 62, respectively The cuboidal fixing block 69 protrudes approximately 3 mm from the top side 59 of the base wall 58. The cuboidal fixing block 69 is made of a plastic material, particularly silicone, and forms a fixation element.

The second clamp jaw 56 has an L-shape and a cuboidal cross-section. The second clamp jaw 56 comprises a long leg 70 and a short leg formed thereon at right angles, said leg being referred to below as the fixation leg 71. The long leg 70 has a base wall 72 and two side walls 73 which define a groove between them.

The end of the long leg 70 which is opposite to the fixation leg 71 is referred to as the joint side 74. A tubular joint body 75 is formed on this joint side 74. The joint body 75 forms a tube having two front sides and a circular opening wherein the length of the tube corresponds to the inner width between the two annular disk members 65. The tubular shaft 67 is arranged in the opening of the joint body. The tubular shaft 67 is rotatably supported in the openings 66 of the annular disk members 65 and in the opening 75 of the joint body 75.

A through hole (not shown) is formed in the fixing leg 71, said hole being in alignment with the groove of the long leg 70. A recess is provided in the tubular joint body 75, said recess being also in alignment with the groove of the long leg 70. The through hole, the groove of the long leg 70 and the recess of the joint body 75 accommodate a fixing tube 77. The fixation tube 77 and/or the fixation element is made of plastic material, particularly silicone.

A latch 78 facing the joint body 75 is formed on the free end of the fixing leg 71. The latch 78 is made so as to grip behind the fixation edge 71 when the two legs are compressed. The latch 78 then locks behind the fixing edge 71 and holds the holding element 8 in a closed state. The latch 78 and the fixation edge thus form a locking member. In the locked state of the holding element, the base jaw 55 and the second clamp jaw 56 are arranged approximately parallel to each other, the fixation block 69 and the fixation tube 77 being pressed onto each other.

The fixation section 3 of a stent 1 can be arranged between the fixation block 55 of the clamp jaw 55 and the fixation tube 77 of the second clamp jaw 56. It is also possible to fix at the same time two fixation sections 3 of two stents with this holding element between the fixation block 69 and a fixation tube 77. Therefore it is useful that the fixation block 69 and the fixation tube 77 each extend over a length of at least 3 to 3 cm.

In the context of this invention it may also be useful to provide such a holding element in a miniaturized embodiment wherein the clamp jaws 55, 56 extend only over a length of e.g. about 1 cm. Two such holding elements then are interconnected with a flexible strip so that with each of the holding elements each one stent can be fixed.

The above described holding elements 8 each are designed for fixation of two stents 1. In the context of the invention it is of course also possible to design a holding element 8 for fixation of only one single stent. Then it is useful that the holding element extends at least in one direction that long that the holding element cannot be pulled into a nostril.

FIG. 10 shows in a schematic representation the stent 1 according to this invention according to FIG. 3 inserted into a nasal cavity 79. The nasal cavity 79 extends from the nasal entry 80 or the nostril 80, respectively, towards the nasopharynx 81. In the region of the nose the nasal cavity is confined by the nasal alar 82. In the nasal cavity two turbinates 83 are present which are arranged between the palate 84 and the 85 ethmoid bone plate 85 of the nasal cavity 79. Between the palate 84 and the inferior turbinate 83 the inferior nasal passage 86 is present, and between the two turbinates 83 a middle nasal passage, and between the upper turbinate 83 and the 85 ethmoid bone plate 85 the upper nasal passage 88.

When the turbinates are swollen then a nasal passage can be kept patent by the use of the stent according to the present invention. The stent 1 is mostly used in the inferior nasal passage. Yet, it is also possible to apply the stent into the middle nasal passage 87 or the upper nasal passage 88, respectively. Especially the inferior nasal passage 86 exhibits a high sensitivity in the posterior part. In this region the support body 2 of the stent 1 should not end as the rear edge 5 may uncomfortably press against the turbinate 83. Therefore, it is useful to arrange the support body in that way that it only splints the anterior part of the nasal passage, or that it extends through the whole nasal passage.

It is also useful that the stent according to the invention is flexible so that it nestles to the shape of the nasal passages. This is realized on the one hand by the elasticity of the wire and on the other hand by the embodiment as a braid.

FIG. 10 shows merely a stent 1 which is fixed by a holding element 8.

In the context of this invention it is possible to use only one single stent. Usually, however, two stents 1 are applied. These two stents normally are the same. For special applications, however, it may be useful to apply two stents of different size (different length and/or diameter and/or construction). Sometimes it may make sense to combine a stent according to this invention for splinting of a nasal passage with a stent for splinting of the airway in the throat as known e.g. from WO 2007/065408 and to use at the same time and to fix with a holding element 8.

LIST OF REFERENCE NUMBERS 1 stent
2 support body
3 fixation section
4 round end
5 crimping body
6 pin
7 ball clutch
8 holding element
9 insertion rod
10 bushing/sleeve
11 opening
12 slit
13 introduction tube
14 introduction tip
15 widened section
16 twisted strand
17 chamfer
18 opening
19 slit
20 longitudinal edge
21 opening
22 opening
23 support wing
24 longitudinal edge
25 stiff enclosure
26 circular section
27 connecting strut
28 connecting region
29 stamping line
30 flexible latch
31 housing
32 insert
33 front wall
34 first recess
35 second recess
36 concave bend
37 longitudinal slit
38 transverse pin
39 spring element
40 first recess
41 second recess
42 concave bend
43 opening
44 opening
45 opening
46 opening
47 frame
48 longitudinal strut
49 longitudinal strut
50 transverse strut
51 transverse strut
52 stamp plate
53 guiding rod
54 spring element
55 first clamp jaw
56 second clamp jaw
57 joint
58 base wall
59 top side
60 bottom side
61 side wall
62 groove
63 joint side
64 lock side
65 annular disk member
66 opening
67 tubular shaft
68 locking edge
69 fixing block
70 long leg
71 fixation leg
72 base wall
73 side wall
74 joint side
75 joint body
76 opening
77 fixation tube
78 latch
79 nasal cavity
80 nasal entry/nostril
81 nasopharynx
82 nasal alar
83 turbinate
84 palate
85 ethmoid bone plate
86 inferior nasal passage
87 middle nasal passage
88 upper nasal passage
89 removal tool
90 tentacle
91 sleeve
92 tentacle
93 polymer drop
94 ring

What is claimed is:

1. A stent for splinting of a nasal passage, comprising:
a braided tubular support body having a proximal end and a distal end, wherein a proximal ending region of the braided tubular support body has a widened section which is about ball-shaped and wherein proximal to the widened section of the tubular support body a fixation section is provided,
wherein the support body and the fixation section are integrally made from one wire braid, and the braid conically tapers within the fixation section,
wherein the stent is braided with a single wire or with a multitude of wires, wherein the single wire or the multitude of wires extends from the proximal end to the distal end and returns back to the proximal end of the support body, whereby the distal end is provided without any individual free wire end, and wherein ends of the single wire or the multitude of wires are connected at the proximal end of the support body, and
wherein the support body, in an unloaded state, has a diameter of at least 4 mm and a length in a range of 25 to 120 mm.

2. The stent of claim 1, wherein the about ball-shaped widened section is oval-shaped.

3. The stent of claim 1, wherein the about ball-shaped widened section has a diameter of at least 10 mm and not exceeding 20 mm.

4. The stent of claim 1, wherein the support body, in the unloaded state, has a diameter not exceeding 20 mm.

5. The stent of claim 1, wherein the support body, in the unloaded state, has a length in a range of 30 to 50 mm.

6. The stent of claim 1, wherein each individual wire has a diameter in a range of from 0.001 to 2 mm.

7. The stent of claim 1, wherein the fixation section comprises a coupling element for fixation of the stent at a holding element and/or an inserting rod.

8. The stent of claim 7, coupled at the coupling element to said holding element and/or inserting rod.

9. The stent of claim 8, positioned within an insertion tube.

10. The stent of claim 1, wherein the about ball-shaped widened section has a diameter of from 12 to 15 mm.

11. The stent of claim 1, wherein the about ball-shaped widened section has a diameter of from 13 to 17 mm.

12. The stent of claim 1, wherein the single wire or the multitude of wires comprises elastic wire.

13. The stent of claim 1, wherein the single wire or the multitude of wires at the distal end of the support body forms a bend that in the unloaded state of the stent has a diameter in a range of from 0.5 to 2 mm.

14. The stent of claim 1, coupled with a removal tool.

15. The stent of claim 1, wherein the stent is braided with the single wire.

16. The stent of claim 1, wherein the stent is braided with the multitude of wires.

17. The stent of claim 1, wherein the single wire or the multitude of wires comprises elastic wire having a diameter of from 0.001 to 2 mm.

18. The stent of claim 1, wherein the single wire or the multitude of wires comprises a metal wire.

19. The stent of claim 1, wherein the single wire or the multitude of wires comprises a nitinol or steel wire.

20. The stent of claim 1, wherein the fixation section in the unloaded state has a length of about 10 to 25 mm.

* * * * *